(12) United States Patent
Lu et al.

(10) Patent No.: US 10,792,374 B2
(45) Date of Patent: Oct. 6, 2020

(54) COMPOSITIONS AND METHODS FOR THE DELIVERY OF NUCLEIC ACIDS

(71) Applicant: CASE WESTERN RESERVE UNIVERSITY, Cleveland, OH (US)

(72) Inventors: Zheng-Rong Lu, Cleveland, OH (US); Da Sun, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/767,119

(22) PCT Filed: Oct. 11, 2016

(86) PCT No.: PCT/US2016/056453
§ 371 (c)(1),
(2) Date: Apr. 9, 2018

(87) PCT Pub. No.: WO2017/062990
PCT Pub. Date: Apr. 13, 2017

(65) Prior Publication Data
US 2019/0091347 A1   Mar. 28, 2019

Related U.S. Application Data

(60) Provisional application No. 62/239,306, filed on Oct. 9, 2015.

(51) Int. Cl.
| | | |
|---|---|---|
| A61K 48/00 | (2006.01) |
| C12N 15/11 | (2006.01) |
| C07D 211/88 | (2006.01) |
| C12N 15/87 | (2006.01) |
| A61K 47/18 | (2017.01) |
| A61K 47/20 | (2006.01) |
| A61P 27/02 | (2006.01) |
| C12N 15/113 | (2010.01) |

(52) U.S. Cl.
CPC .......... *A61K 48/0033* (2013.01); *A61K 47/18* (2013.01); *A61K 47/20* (2013.01); *A61K 48/0075* (2013.01); *A61P 27/02* (2018.01); *C07D 211/88* (2013.01); *C12N 15/111* (2013.01); *C12N 15/113* (2013.01); *C12N 15/87* (2013.01); *C12N 2320/32* (2013.01)

(58) Field of Classification Search
CPC . A61K 48/0033; A61K 48/0075; A61P 27/02; C07D 211/88; C12N 15/111; C12N 15/113; C12N 15/87; C12N 2320/32

USPC ................................................. 435/455, 458
See application file for complete search history.

(56) References Cited

U.S. PATENT DOCUMENTS

| | | | |
|---|---|---|---|
| 8,686,052 B2 | 4/2014 | Niitsu et al. |
| 9,066,982 B2 | 6/2015 | Brahmbhatt et al. |
| 9,957,224 B2 | 5/2018 | Bavik et al. |
| 2008/0275134 A1* | 11/2008 | Palczewski ............ A61K 31/07 514/725 |
| 2013/0245107 A1 | 9/2013 | De Fougerolles et al. |

FOREIGN PATENT DOCUMENTS

| | | | | |
|---|---|---|---|---|
| WO | 2005/105155 A1 | 11/2005 | | |
| WO | WO-2005105155 A1 * | 11/2005 | ............ | C12N 15/86 |

OTHER PUBLICATIONS

Malamas et al. Journal of Control Release, vol. 17, No. 3, pp. 296-307, pp. 1-32. (Year: 2013).*
Rajala et al. Nan. Lett., vol. 14, pp. 5257-5263. (Year: 2014).*
Malamas et al. "Design and Evaluation of New pH-Sensitive Amphiphilic Cationic Lipids for siRNA Delivery", J Control Release. 2013, vol. 171(3). pp. 296-307, pp. 1-32.
Rajala et al. "Nanoparticle-Assisted Targeted Delivery of Eye-Specific Genes to Eye:i Significantly Improve:i the Vi: Jion of Blind Mice In Vivo", Nano Lett., 2014, vol. 14, pp. 5257-5263.

* cited by examiner

*Primary Examiner* — Janet L Epps-Smith
(74) *Attorney, Agent, or Firm* — Tarolli, Sundheim, Covell & Tummino LLP

(57) ABSTRACT

A compound comprising formula (I): wherein R1 is an alkylamino group or a group containing at least one aromatic group; R2 and R3 are independently an aliphatic group or hydrophobic group; R4 and R5 are independently H, a substituted or unsubstituted alkyl group, an alkenyl group, an acyl group, or an aromatic group, or includes a polymer, a targeting group, or a detectable moiety, and at least one of R4 and R5 includes a targeting group that targets and/or binds to a retinal or visual protein; a, b, c, and d are independently an integer from 1 to 10; and pharmaceutically acceptable salts thereof.

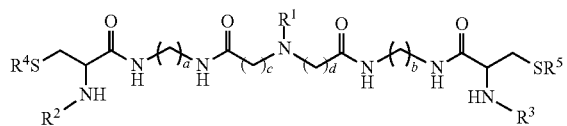

18 Claims, 7 Drawing Sheets

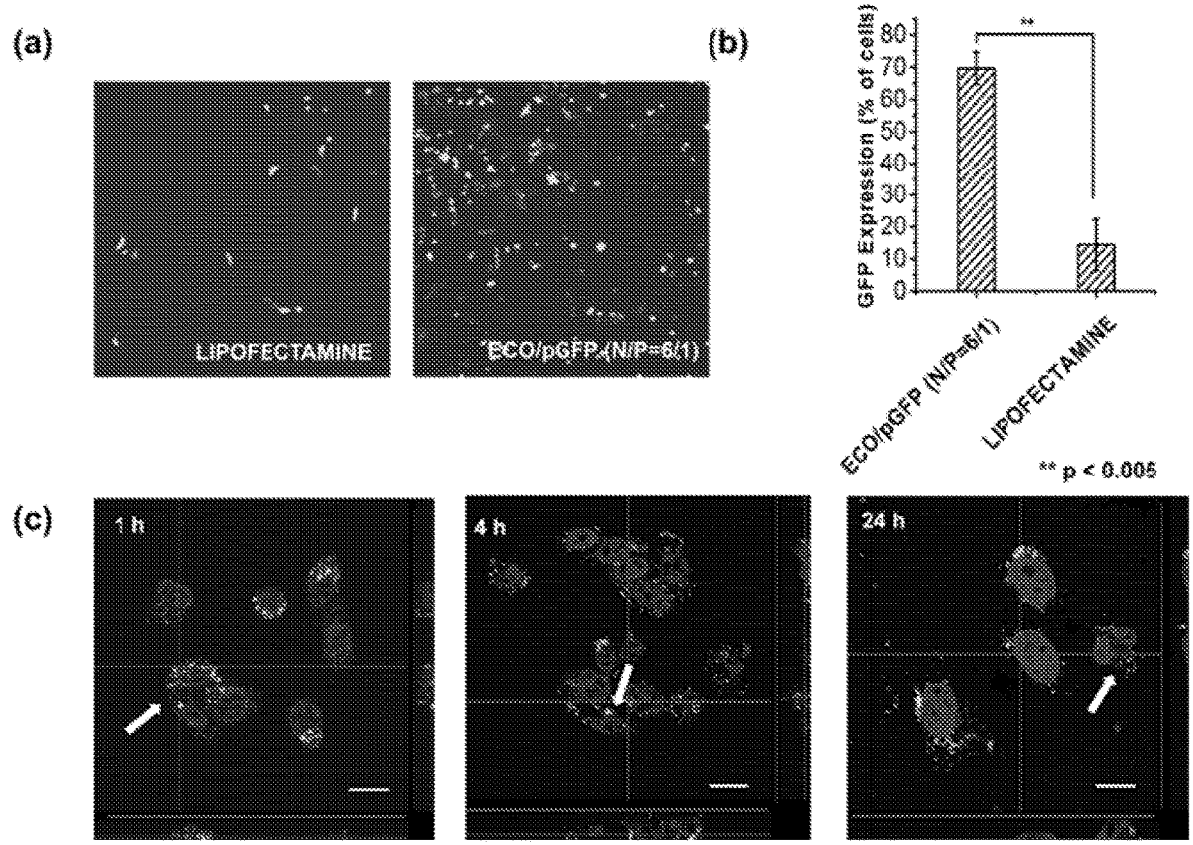
Figs. 1A-C

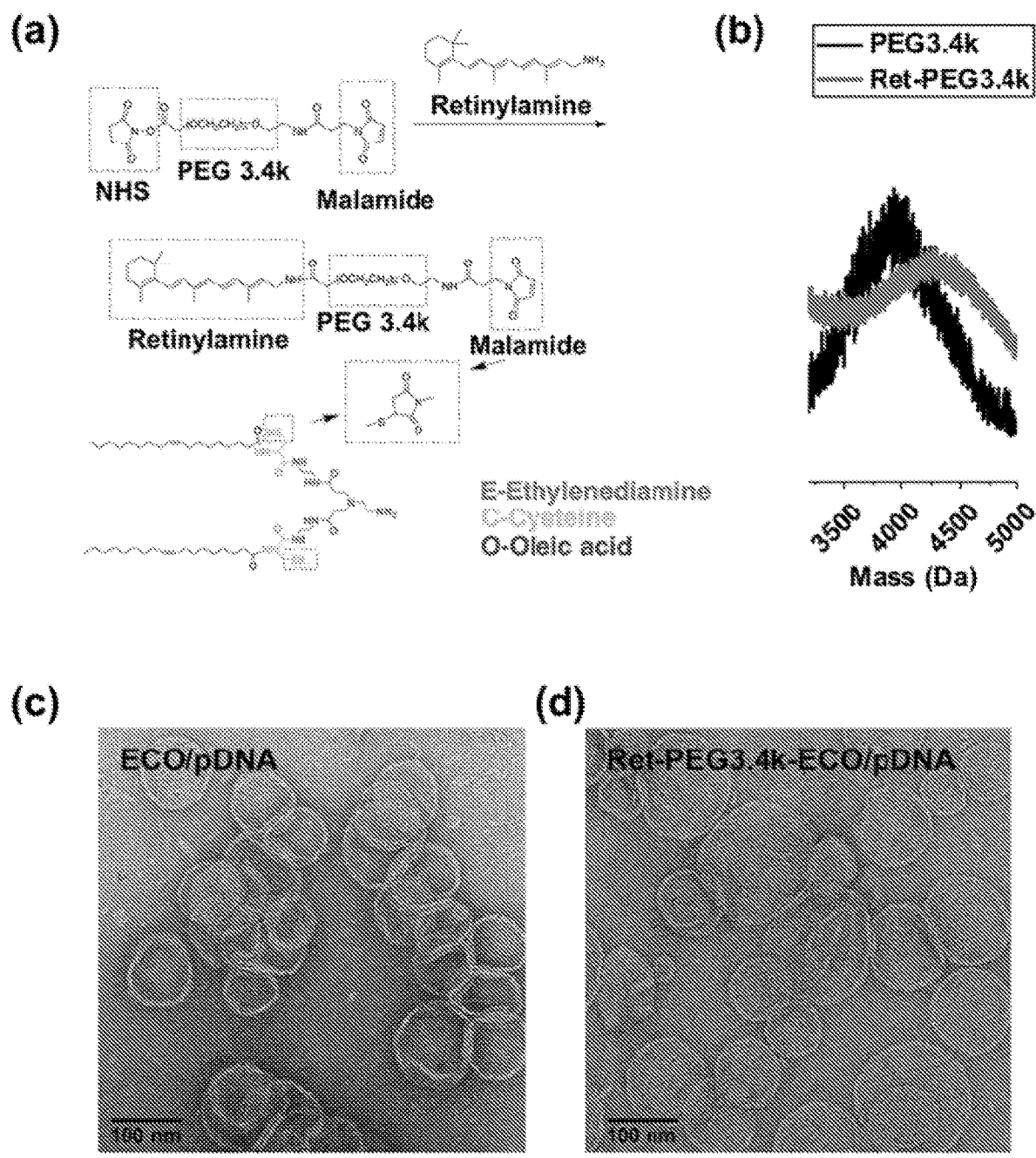
Figs. 2A-D (a)
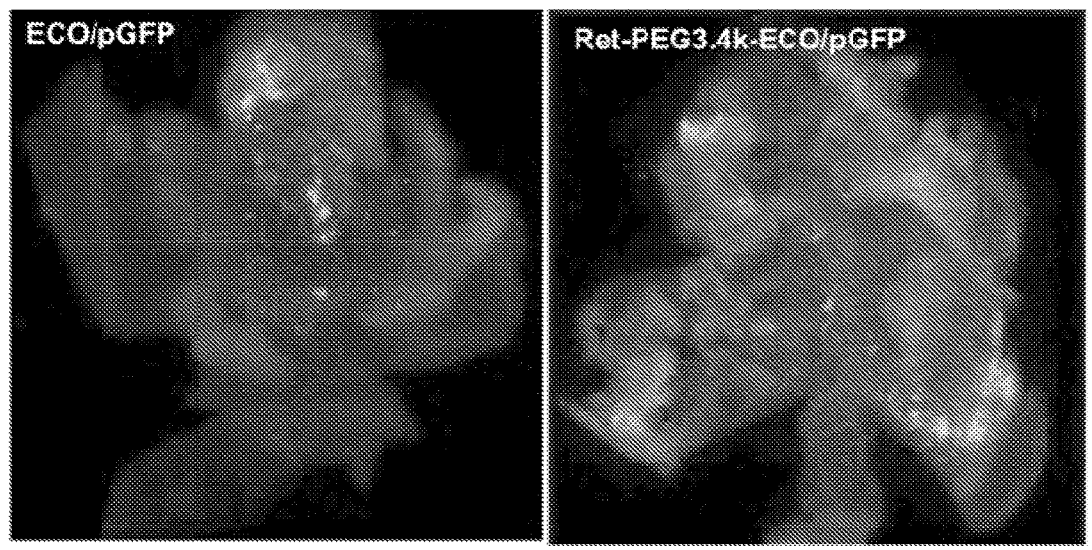
(b)
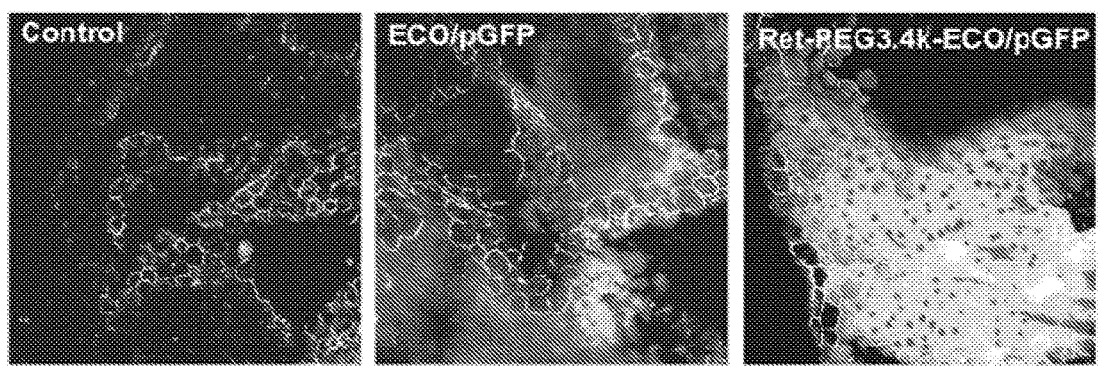
Figs. 3A-B

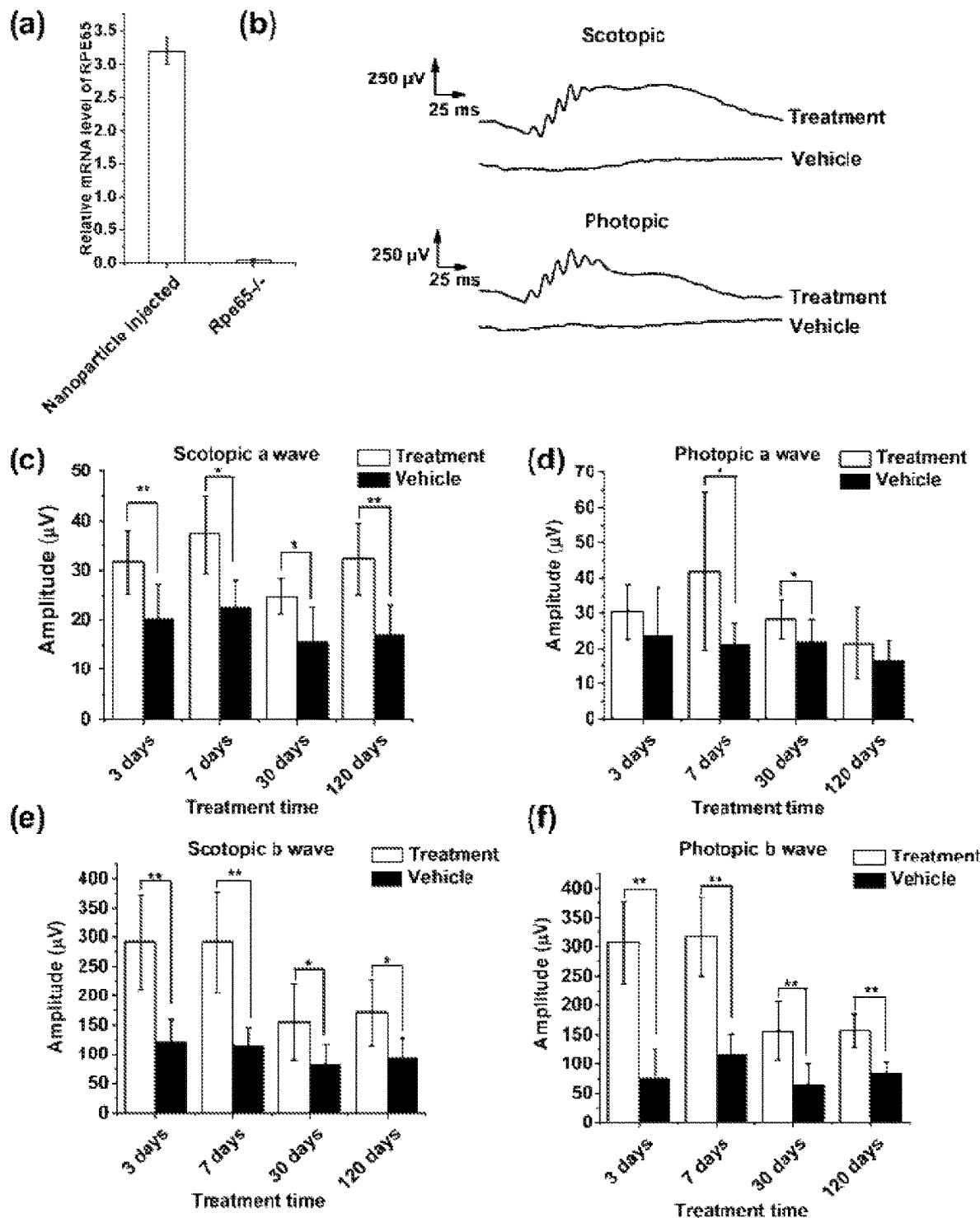
Figs. 4A-F

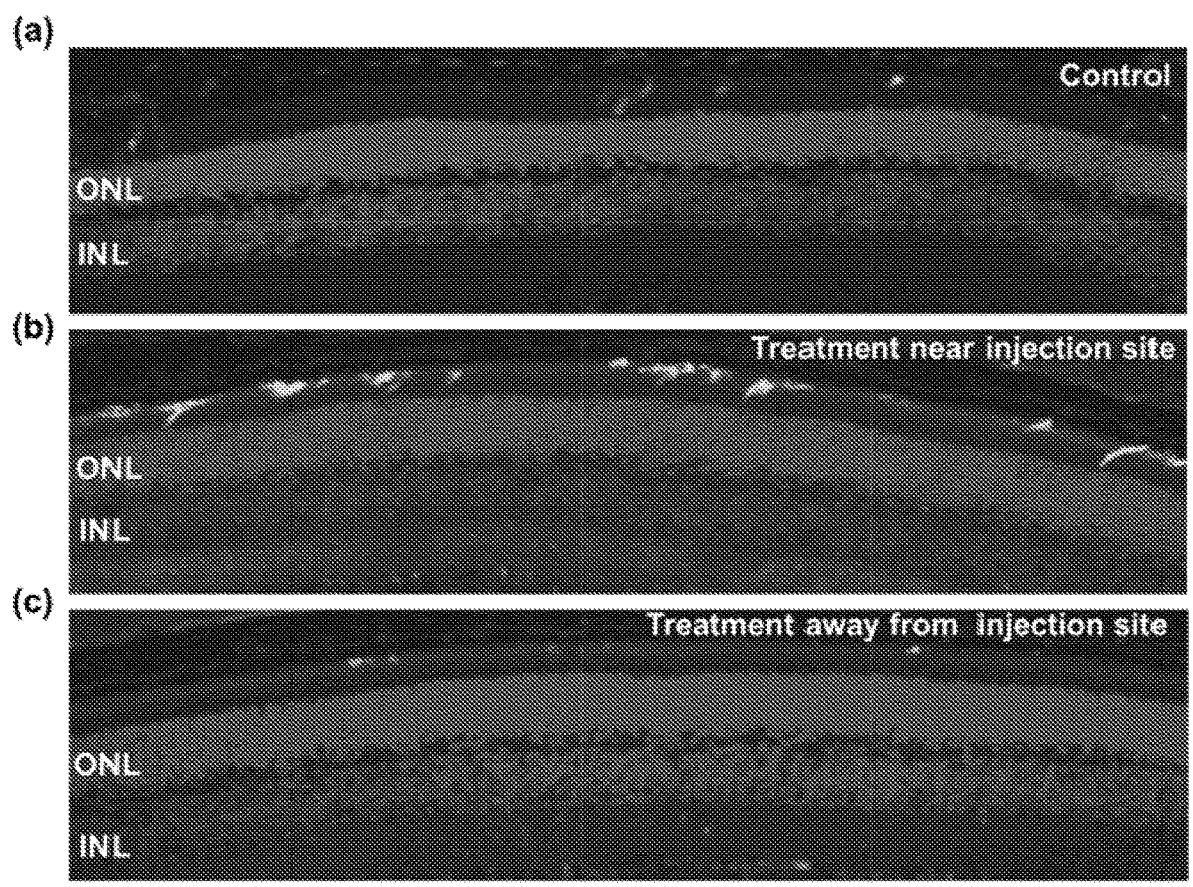
Figs. 5A-C

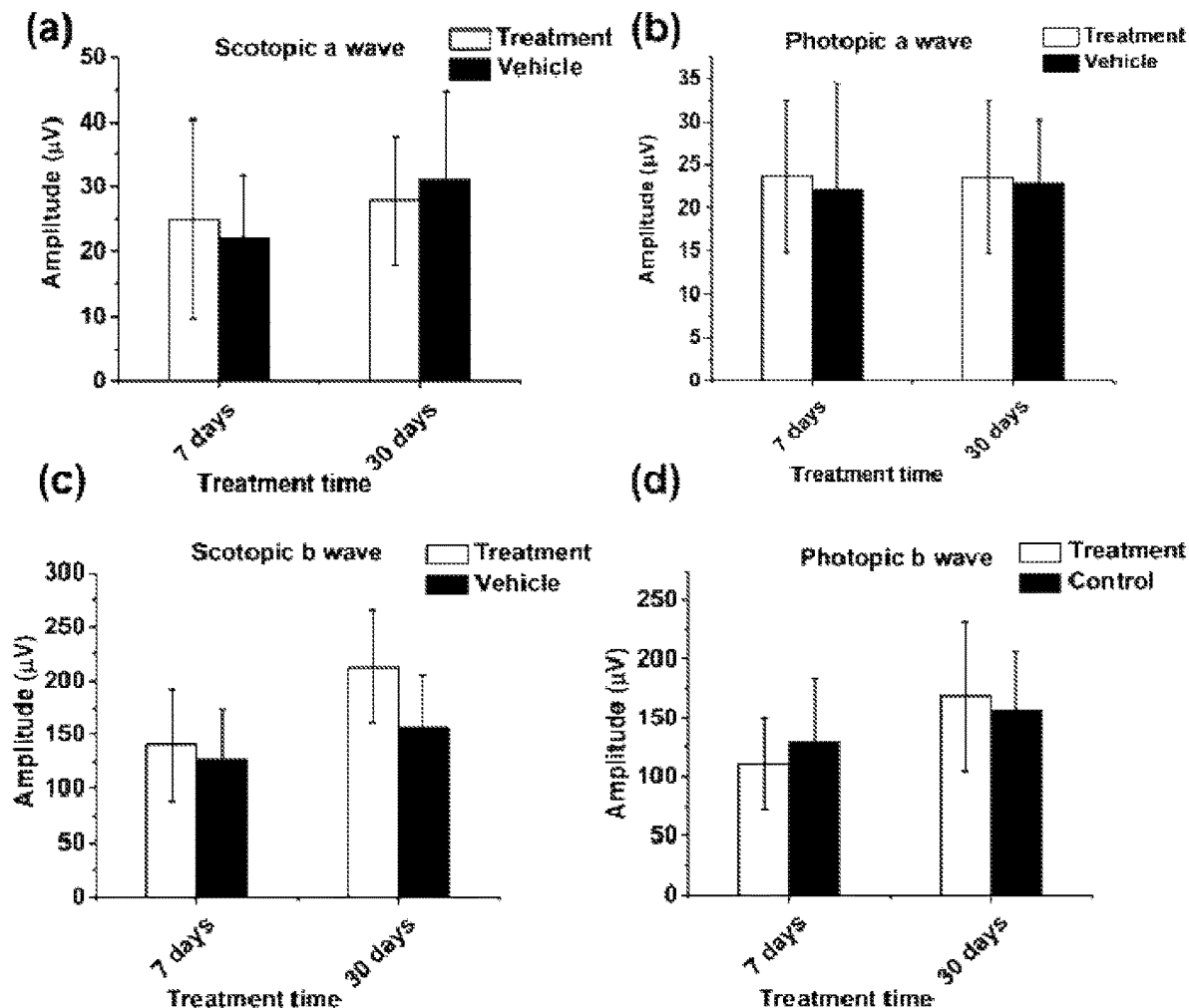
Figs. 6A-D

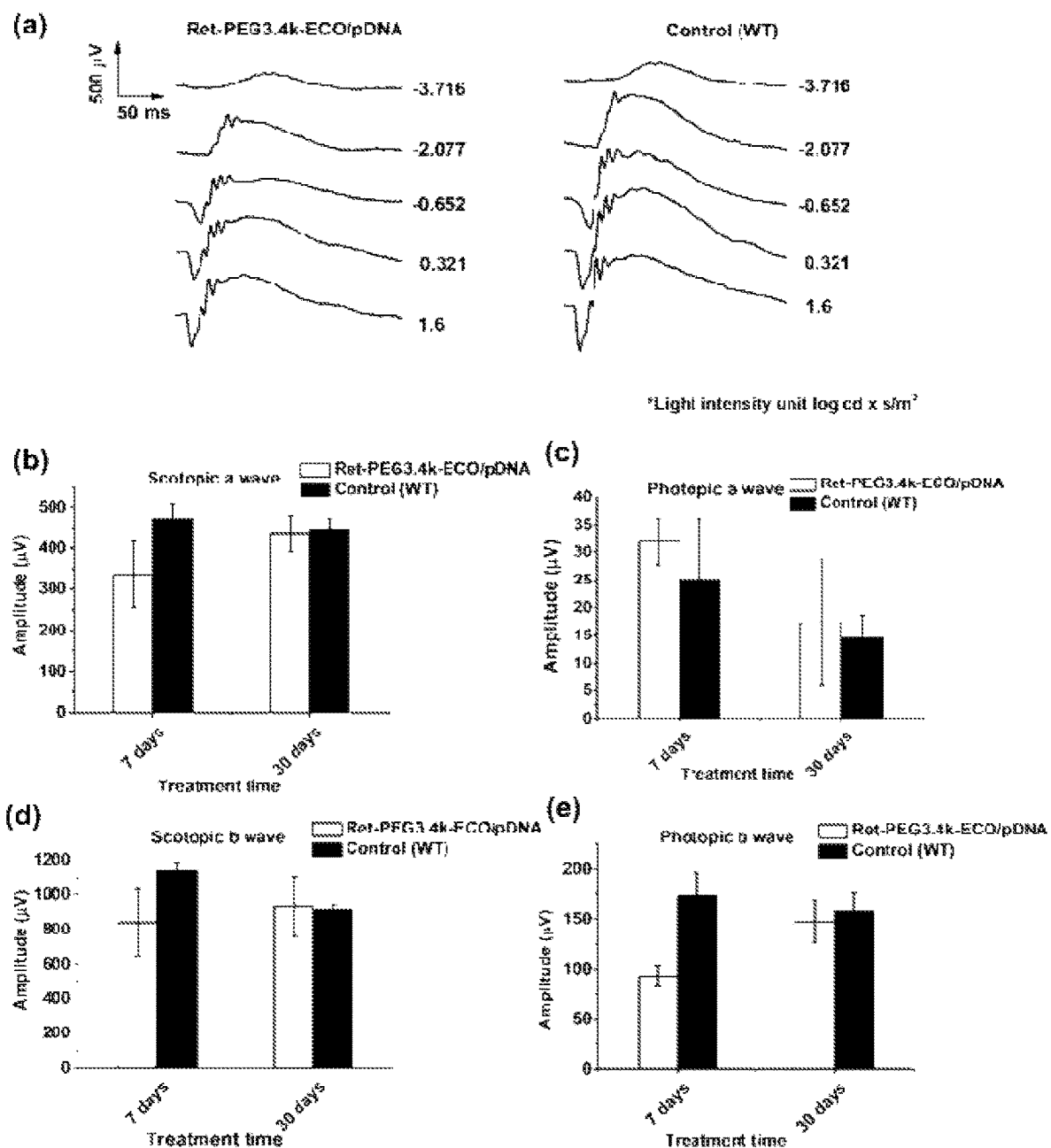
Figs. 7A-E

COMPOSITIONS AND METHODS FOR THE DELIVERY OF NUCLEIC ACIDS

RELATED APPLICATION

This application claims priority from U.S. Provisional Application No. 62/239,306, filed Oct. 9, 2015, the subject matter of which is incorporated herein by reference in its entirety.

GOVERNMENT FUNDING

This invention was made with government support under Grant No. EB00489 awarded by The National Institutes of Health and Grant Number DGE-0951783, awarded by the National Science Foundation Graduate Research Fellowship. The United States government has certain rights to the invention.

BACKGROUND

The eye is an attractive target for gene therapy strategies due to its accessibility and immune-privileged characteristics, which will minimize the inflammatory and immune reactions when local gene therapy is applied. However, gene delivery to the eye is never an easy task, because there are multiple obstacles in the way of genetic therapeutics to their destination. Retina is separated into ten layers and each of them has vital functions in the process of photoreception/transduction processes. Genetic eye disorders in each specific layers can cause different phenotypes. Therefore, gene therapies for these disorders require not only high transfection efficiency but also high specificity, because therapies without high specificity will introduce exogenous functional gene to undesired tissue, which will in turn result in potential disorders of vision.

Non-viral systems that employ cationic lipids, dendrimers, polycations and polysaccharides have been developed for gene delivery. Non-viral systems generally exhibit advantages of the ease of production, good safety profiles, and unlimited cargo capacity. However, their clinical translation is hindered by their low transfection efficiency and transient gene expression. Novel design of highly effective non-viral delivery systems is needed to overcome the limitations of the existing non-viral delivery systems for effective gene therapy of visual disorders.

SUMMARY

Embodiments described herein relate to compounds used to form multifunctional pH-sensitive carriers or nanoparticles that are designed to condense therapeutic nucleic acids and deliver the condensed nucleic acids to cells of the eye. The compounds can include a protonable amino head group, which can complex with the nucleic acids, fatty acid or lipid tails, which can participate in hydrophobic condensation, two cysteine residues capable of forming disulfide bridges via autooxidation, and a targeting group that targets and/or binds to a retinal or visual protein, such as an interphotoreceptor retinoid binding protein.

In some embodiments, the compound includes formula (I):

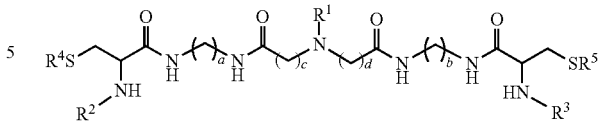

wherein $R^1$ is an alkylamino group or a group containing at least one aromatic group; $R^2$ and $R^3$ are independently an aliphatic group or a hydrophobic group derived, for example, from a fatty acid; $R^4$ and $R^5$ are independently H, a substituted or unsubstituted alkyl group, an alkenyl group, an acyl group, or an aromatic group, or includes a polymer, a targeting group, or a detectable moiety and at least one of $R^4$ and $R^5$ includes a targeting group that targets and/or binds to a retinal or visual protein, such as an interphotoreceptor retinoid binding protein; a, b, c, and d are independently an integer from 1 to 10 (e.g., a, b, c, and d are each 2); and pharmaceutically acceptable salts thereof.

In some embodiments, $R^1$ can include at least one of:

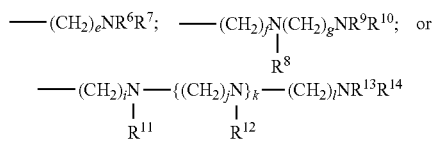

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10. For example, $R^1$ can include at least one of $CH_2CH_2NH_2$, $CH_2CH_2NHCH_2CH_2NHCH_2CH_2NH$, or $CH_2CH_2NHCH_2CH_2CH_2CH_2NHCH_2CH_2NH$.

In other embodiments, $R^2$ and $R^3$ are independently a hydrophobic group derived from oleic acid or linoleic acid and are the same or different.

In other embodiments, the targeting group that targets and/or binds to an interphotoreceptor retinoid binding protein can be covalently attached to a thiol group of a cysteine residue of the compound by a linker. For example, the targeting group can include a retinoid or retinoid derivative, such as all-trans-retinylamine or (1R)-3-amino-1-[3-(cyclohexylmethoxy)phenyl]propan-1-ol; hydrochloride, that is conjugated to a linker, such as a polyethylene glycol linker, which is covalently bound to the thiol group of a cysteine residue of the compound.

In some embodiments, a therapeutic nucleic acid can be complexed with the compound to form multifunctional pH-sensitive carriers or nanoparticles that can be administered to the eye of a subject in need thereof. The therapeutic nucleic acid can include any nucleic acid that when complexed with the compound and introduced to or within the eye is capable of treating, ameliorating, attenuating, and/or eliminating symptoms of a disease or disorder of the eye.

BRIEF DESCRIPTION OF THE DRAWINGS

FIGS. 1(A-C) illustrate images and a graph showing in vitro transfection of ARPE19 cells with ECO/pDNA nanoparticles. (A) Confocal microscopy images and (B) flow cytometry analysis of ARPE19 cells transfected with ECO/pGFP (N/P=6) nanoparticles and Lipofectamine 2000/pGFP nanoparticles for 48 hours (**p<0.005). (C) Confocal fluorescence microscopic images demonstrating intracellular trafficking of ECO/Cy3-pDNA nanoparticles in ARPE-19 cells. Cells were treated with LysoTracker Green (1:2500 dilution) and Hoechst 33342 (1:10000 dilution) and then transfected with ECO/Cy3-labeled nanoparticles at N/P=6. After 1, 4 and 24 h of transfection, cells were fixed and imaged. Arrows denote the ECO/Cy3-pDNA nanoparticles. Scale bar is 20 μm.

FIGS. 2(A-D) illustrate synthesis and MALDI-TOF mass spectrum of Ret-PEG-MAL and TEM images of Ret-PEG-ECO/pDNA nanoparticles. Nanoparticles were prepared by depositing 20 μL of the particle solution onto a 300-mesh copper grid covered by a thin amorphous carbon film (20 nm). Samples were stained twice by the addition of 3 μL of 2% uranyl acetate aqueous solution.

FIGS. 3(A-B) illustrate images showing in vivo gene transfection with targeted Ret-PEG-ECO/pGFP nanoparticles in wild type BALB/c mice. Mice (1-month-old) were subretinally injected with ECO/pGFP or Ret-PEG-ECO/pGFP nanoparticles. RPE flat mounts were obtained 3 days post transfection. (A) Fluorescence microscopic images show enhanced GFP expression with Ret-PEG-ECO/pGFP nanoparticles in the RPE 3-days post injection. (B) Confocal fluorescence microscopic images show GFP expression specifically in the RPE with anti-ZO-1 antibody staining (white). The tight junction protein ZO-1 represents the borders of the RPE cells.

FIGS. 4(A-F) illustrate graphs and a plot showing gene replacement therapy using Ret-PEG-ECO/pRPE65 nanoparticles in rpe65$^{-/-}$ mice. The mice were subretinally injected with Ret-PEG-ECO/pRPE65 nanoparticles or Ret-PEG-ECO. (A) Relative RPE65 mRNA level in treated (pRPE65 injected) and control groups 15 days after treatment. (B) Representative scotopic and photopic electroretinograms acquired in rpe65$^{-/-}$ mice under the intensity of 1.6 log cd×s/m$^2$ at 7 days after the treatment Amplitudes of (C) scotopic a-waves, (D) photopic a-waves, (E) scotopic b-waves and (F) photopic b-waves of treated and control rpe65$^{-/-}$ mice at 3, 7, 30 and 120 days post injection.

FIGS. 5(A-C) illustrate images showing cone preservation after gene replacement therapy using Ret-PEG-ECO/pRPE65 nanoparticles in rpe65 mice 120 days after treatment. Peanut agglutinin was used to stain cone photoreceptors. Nuclei were stained with DAPI.

FIGS. 6(A-D) illustrate graphs showing the therapeutic effect of gene replacement therapy using Ret-PEG-ECO/pRPE65 nanoparticles in 3-month-old rpe65$^{-/-}$ mice. ERG amplitudes of major response waveforms (A) scotopic a-waves, (B) photopic a-waves, (C) scotopic b-waves and (D) photopic b-waves in the treatment and control groups of rpe65$^{-/-}$ mice.

FIGS. 7(A-E) illustrate plots and graphs showing safety assessment of Ret-PEG-ECO/pRPE65 nanoparticles in BALB/c mice (1-month-old). (A) Representative ERG traces of scotopic waveforms in the PEG-ECO/pRPE65 treated group and untreated mice at 30 days post-injection. ERG amplitudes of amplitudes of (B) scotopic a-waves, (C) photopic a-waves, (D) scotopic b-waves, and (E) photopic b-waves in treated and control mice.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

The term "alkenyl group" is defined herein as a $C_2$-$C_{20}$ alkyl group possessing at least one C=C double bond.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "acyl" group as used herein is represented by the formula C(O)R, where R is an organic group such as, for example, an alkyl or aromatic group as defined herein.

The term "alkylene group" as used herein is a group having two or more $CH_2$ groups linked to one another. The alkylene group can be represented by the formula $(CH_2)_a$, where a is an integer of from 2 to 25.

The term "aromatic group" as used herein is any group containing an aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The phrase "nitrogen containing substituent" is defined herein as any amino group. The term "amino group" is defined herein as a primary, secondary, or tertiary amino group. In the alternative, the nitrogen containing substituent can be a quaternary ammonium group. The nitrogen containing substituent can be an aromatic or cycloaliphatic group, where the nitrogen atom is either part of the ring or directly or indirectly attached by one or more atoms (i.e., pendant) to the ring. The nitrogen containing substituent can be an alkylamino group having the formula $RNH_2$, where R is a branched or straight alkyl group, and the amino group can be substituted or unsubstituted.

The term "nucleic acid" refers to oligonucleotides, nucleotides, polynucleotides, or to a fragment of any of these, to DNA or RNA (e.g., mRNA, rRNA, tRNA, miRNA, siRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids containing known analogues of natural nucleotides, as well as nucleic acid-like structures with synthetic backbones.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

Embodiments described herein relate to compounds used to form multifunctional pH-sensitive carriers or nanoparticles that are designed to condense therapeutic nucleic acids and deliver the condensed nucleic acids to cells of the eye. The compounds can include a protonable amino head group, which can complex with the nucleic acids, fatty acid or lipid tails, which can participate in hydrophobic condensation, two cysteine residues capable of forming disulfide bridges via autooxidation, and a targeting group that targets and/or binds to a retinal or visual protein, such as an interphotoreceptor retinoid binding protein.

The protonable amino head group can complex with therapeutic nucleic acids to form multifunctional pH-sensitive carriers or nanoparticles for delivery of nucleic acids to cells of the eye. The amines in the head groups contribute to the essential pH-sensitive characteristic of the carrier system, which is important for improving endosomal escape of the nucleic acid. Greater protonation of the amino head groups can occur in the relatively acidic environment (pH=5-6) of the endosome and lysosome compartments after cellular uptake. This enhances electrostatic interactions between the cationic carriers and the anionic phospholipids of endosomal/lysosomal membranes, promoting the bilayer destabilization and nanoparticle charge neutralization events required for efficient cytosolic release of their nucleic acid payload. By affecting the number of amines, and thus overall pKa, of the cationic carrier, the choice of head group can ultimately determine the degree to which such protonation can occur. The pH-sensitive property of the carrier system is essential so that the nanoparticles do not affect the integrity of the outer cell membrane and cause cell death, but instead are able to selectively fuse with and destabilize the endosomal and lysosomal membranes.

The cysteine residues can form disulfide bridges via autooxidation and react with functional groups of other compounds, such as those containing thiol groups. Once the nucleic acid is complexed with the compound to form the multifunctional pH-sensitive carriers or nanoparticles, the thiol groups can produce disulfide (S—S) bonds or bridges by autooxidation to form oligomers and polymers or cross-linking. The disulfide bonds can stabilize the nanoparticles of the nucleic acid and compound and help achieve release of the nucleic acid once the nanoparticle is in the cell.

For example, when the nucleic acid is siRNA, the cleavage of disulfide bonds in the siRNA delivery systems in reductive cytoplasm can facilitate cytoplasm-specific release of siRNA. The multifunctional pH-sensitive carriers or nanoparticles comprising the compounds are stable in the plasma at very low free thiol concentration (e.g., 15 µM). When the compounds are incorporated into target cells, the high concentration of thiols present in the cell (e.g., cytoplasm) will reduce the disulfide bonds to facilitate the dissociation and release of the nucleic acid.

The disulfide bonds can be readily produced by reacting the same or different compounds before complex with the nucleic acids or during the complex in the presence of an oxidant. The oxidant can be air, oxygen or other chemical oxidants. Depending upon the dithiol compound selected and oxidative conditions, the degree of disulfide formation can vary in free polymers or in complexes with nucleic acids. Thus, the compounds including two cysteine residues are monomers, and the monomers can be dimerized, oligomerized, or polymerized depending upon the reaction conditions.

The fatty acid or lipid tails groups can participate in hydrophobic condensation and help form compact, stable nanoparticles with the nucleic acids and introduce amphiphilic properties to facilitate pH sensitive escape of nanoparticles from endosomal and lysosomal compartments. This is particularly useful when the compounds are used as in vivo delivery devices.

In general, the transfection efficiency of carriers has been shown to decrease with increasing alkyl chain length and saturation of the lipid tail groups. When saturated, shorter aliphatic chains (C12 and C14) favor higher rates of inter-membrane lipid mixing and reportedly allow for better transfection efficiencies in vitro, as compared to in vivo, whereas the opposite is true for longer chains (C16 and C18). Typically, saturated fatty acids greater than 14 carbons in length are not favorable for nucleic acid transfections due to their elevated phase transition temperature and overall less fluidity than those that are unsaturated. However, it has been discovered that there exists a limit, at which point an increase in unsaturation and lipid fluidity is inversely correlated to transfection efficiency, primarily because some degree of rigidity is required for particle stability, as evidenced by the widespread use of cholesterol in lipid nanoparticle formulations.

In some embodiments, the targeting group that targets and/or binds to a retinal or visual protein, such as an interphotoreceptor retinoid binding protein, can be attached to a cysteine residue of the compound by, for example, a thiol group of the cysteine residue. The targeting group can include, for example, a retinoid, such as a retinylamine (e.g., all-trans-retinylamine) or retinoid derivative, such as (1R)-3-amino-1-[3-(cyclohexylmethoxy)phenyl]propan-1-ol; hydrochloride. In some embodiments, the targeting group is all-trans-retinylamine. In other embodiments, the targeting group is (1R)-3-amino-1-[3-(cyclohexylmethoxy)phenyl]propan-1-ol; hydrochloride. In still other embodiments, the targeting group is a synthetic retinoid derivative, such as a synthetic retinoid derivative described in U.S. Pat. No. 7,951,841 or 7,982,071 and PCT/US2015/062343 all of which are incorporated by reference in their entirety.

For example, the targeting group can include a primary amine compound of formula:

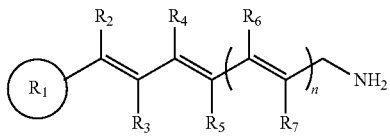

wherein $R_1$ is a cyclic or polycyclic ring, wherein the ring is a substituted or unsubstituted aryl, heteroaryl, cycloalkyl, or heterocyclyl;

n=1-3;

wherein $R_2$, $R_3$, $R_4$, $R_5$, $R_6$, and $R_7$, are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, –Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof, wherein, $R_2$ and $R_4$ may be linked to form a cyclic or polycyclic ring, wherein the ring is a substituted or unsubstituted aryl, heteroaryl, cycloalkyl, or heterocyclyl; and pharmaceutically acceptable salts thereof.

The targeting group can be conjugated directly to the thiol group of the cysteine residue of the compound or indirectly via a linker (e.g., polyethylene glycol) prior or during the formation of nanoparticles. Depending upon the selection of the targeting group, the targeting group can be covalently bonded to either the thiol group of the cysteine residues.

In one aspect, the targeting group is indirectly attached to the compound by a linker. Examples of linkers include, but are not limited to, a polyamine group, a polyalkylene group, a polyamino acid group or a polyethylene glycol group. The selection of the linker as well as the molecular weight of the linker can vary depending upon the desired properties. In one aspect, the linker is polyethylene glycol having a molecular weight from 500 to 10,000, 500 to 9,000, 500 to 8,000, 500 to 7,000, or 2,000 to 5,000. In certain aspects, the targeting group is first reacted with the linker in a manner such that the targeting group is covalently attached to the linker. For example, the linker can possess one or more groups that can react with an amino group present on a targeting group. The linker also possesses additional groups that react with and form covalent bonds with the compounds described herein. For example, the linker can possess maleimide groups that readily react with the thiol groups. The selection of functional groups present on the linker can vary depending upon the functional groups present on the compound and the targeting group. In one aspect, the targeting group is a retinoid, such as a retinylamine (e.g., all-trans-retinylamine) or retinoid derivative, such as (1R)-3-amino-1-[3-(cyclohexylmethoxy)phenyl]propan-1-ol; hydrochloride, that is covalently attached to polyethylene glycol.

In some embodiment, the linker can include an acid labile bond, such as formed by incorporation of a hydrazone into the linker that is hydrolyzable in an endolysomal environment following uptake to cells, such as retinal or retinal pigment epithelium cells. For example, the linker can be covalently linked to the compound by at least one of a covalent hydrolyzable ester, covalent hydrolyzable amide, covalent photodegradable urethane, covalent hydrolyzable ester, or covalent hydrolyzable acrylate-thiol linkage. Following cellular uptake of the compound, within the late endosomes, the increasingly acidic environment can cleave the acid labile linkage to promote shedding of a polymer linker, such as PEG, and expose the core of the compound/nucleic complex nanoparticle.

In some embodiments, the compound used to form the multifunctional pH-sensitive carriers or nanoparticles can have formula (I):

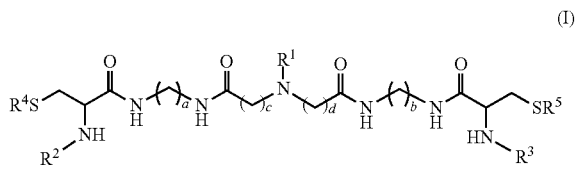

wherein $R^1$ is an alkylamino group or a group containing at least one aromatic group; $R^2$ and $R^3$ are independently an aliphatic group or a hydrophobic group, derived, for example, from a fatty acid;

$R^4$ and $R^5$ are independently H, a substituted or unsubstituted alkyl group, an alkenyl group, an acyl group, or an aromatic group, or includes a polymer, a targeting group, or a detectable moiety and at least one of $R^4$ and $R^5$ includes a targeting group that targets and/or binds to a retinal or visual protein, such as an interphotoreceptor retinoid binding protein; a, b, c, and d are independently an integer from 1 to 10 (e.g., a, b, c, and d are each 2); and pharmaceutically acceptable salts thereof.

In some embodiments, $R^1$ can include at least one of:

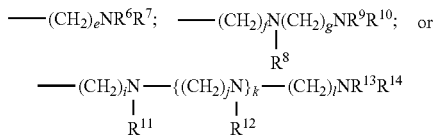

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10.

For example, $R^1$ can include at least one of $CH_2NH_2$, $CH_2CH_2NH_2$, $CH_2CH_2CH_2NH_2$, $CH_2CH_2CH_2CH_2NH_2$, $CH_2CH_2CH_2CH_2CH_2NH_2$, $CH_2NHCH_2CH_2CH_2NH_2$, $CH_2CH_2NHCH_2CH_2CH_2NH_2$, $CH_2CH_2CH_2NHCH_2CH_2CH_2NHCH_2CH_2CH_2NH_2$, $CH_2CH_2NHCH_2CH_2CH_2NH_2$, $CH_2CH_2NHCH_2CH_2CH_2NHCH_2CH_2CH_2HN_2$, or $CH_2CH_2NH(CH_2CH_2NH)_dCH_2CH_2NH_2$, where d is from 0 to 10.

In some embodiments, $R^1$ can be $CH_2CH_2NH_2$ or $CH_2CH_2NHCH_2CH_2CH_2NHCH_2CH_2CH_2HN_2$.

In other embodiments, $R^2$ and $R^3$ are independently an aliphatic group or a hydrophobic group derived from fatty acid, such as oleic acid or linoleic acid, and are the same or different. The additional double bond in linoleic acid introduces an extra kink into the hydrocarbon backbone, giving the compound a broader conical shape than oleic acid and increasing its fluidity. When incorporated into a nanoparticle structure, the extra degree of unsaturation elevates the propensity to form the hexagonal phase during an impending membrane fusion event of cellular uptake.

In some embodiments, at least one of $R^4$ or $R^5$ includes a retinoid, such as a retinylamine (e.g., all-trans-retinylamine) or retinoid derivative, such as (1R)-3-amino-1-[3(cyclohexylmethoxy)phenyl]propan-1-ol; hydrochloride, that is covalently attached to a polymer linker, such as polyethylene glycol.

The compounds having the general formula I can be synthesized using solid phase techniques known in the art. The Example provides exemplary synthetic procedures for preparing the compounds. In general, the approach in the Example involves the systematic protection/elongation/deprotection to produce a dithiol compound. The hydrophobic group is produced by reacting oleic acid with the amino group present on the cysteine residue. The targeting group is conjugated to a PEG spacer and then conjugated to the compound via a Michael addition reaction. Although the Example depicts one approach for producing the compounds of formula I, other synthetic techniques can be used.

Any of the compounds described herein can exist or be converted to the salt thereof. In one aspect, the salt is a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of the compound to base used is chosen to provide the ratio desired for any particular salts. For preparing, for example, the ammonium salts of the free acid starting material, the starting material can be treated with approximately one equivalent of base to yield a salt.

In another aspect, any of the compounds described herein can exist or be converted to the salt with a Lewis base thereof. The compounds can be treated with an appropriate amount of Lewis base. Representative Lewis bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, THF, ether, thiol reagent, alcohols, thiol ethers, carboxylates, phenolates, alkoxides, water, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular complexes. For example, the ammonium salts of the free acid starting material, the starting material can be treated with approximately one equivalent of chemically or pharmaceutically acceptable Lewis base to yield a complex.

If the compounds possess carboxylic acid groups, these groups can be converted to pharmaceutically acceptable esters or amides using techniques known in the art. Alternatively, if an ester is present on the dendrimer, the ester can be converted to a pharmaceutically acceptable ester using transesterification techniques.

The therapeutic nucleic acid that complexes with and are condensed by the compounds described herein to form the multifunctional pH-sensitive carriers or nanoparticles can include any nucleic acid that when introduced to or within the eye is capable of treating, ameliorating, attenuating, and/or eliminating symptoms of a disease or disorder of the eye. The nucleic acid can be any nucleic acid encoding a natural, truncated, artificial, chimeric or recombinant product [e.g., a polypeptide of interest (including a protein or a peptide), a RNA, etc.] that is capable of treating, ameliorating, attenuating, and/or eliminating symptoms of a disease or disorder of the eye.

The nucleic acid can be a deoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). The nucleic acid may be single stranded or multistranded nucleic acid, double-stranded nucleic acid or may be complexed. The nucleic acid may comprise hybrid sequences or synthetic or semi-synthetic sequences. It may be obtained by any technique known to persons skilled in the art, and especially by screening libraries, by chemical synthesis, or alternatively by mixed methods including chemical or enzymatic modification of sequences obtained by screening libraries.

In a particular embodiment, the therapeutic nucleic acid is of synthetic or biosynthetic origin, or extracted from a virus or from a unicellular or pericellular eukaryotic or prokaryotic organism.

The therapeutic nucleic acid used may be naked, may be complexed with any chemical, biochemical or biological agent, may be inserted in a vector, etc., when administered to the eye.

The naked DNA can refer to any nucleic acid molecule which is not combined with a synthetic, biosynthetic, chemical, biochemical or biological agent improving the delivery or transfer of said DNA, or facilitating its entry into the cell.

The vector can be a nucleic acid molecule that is capable of transporting another nucleic acid to which it has been linked. In some embodiments, the vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form, are not bound to the chromosome. In some embodiments, the plasmid can be the most commonly used form of vector. In other embodiments, the plasmid can be a form of naked DNA as described herein.

In some embodiment, the nucleic acid may also contain one or more additional regions, for example regulatory elements of small or large size which are available to the skilled artisan such as a promoter region (constitutive, regulated, inducible, tissue-specific, etc.), for example sequences allowing and/or promoting expression in the targeted tissue (e.g., choroid or retina) or cells (e.g., RPE or photoreceptors), a transcription termination signal, secretion sequences, an origin of replication and/or nuclear localization signal (nls) sequences which further enhance polynucleotide transfer to the cell nucleus.

Additionally, the nucleic acid may further comprise selectable markers useful in selecting, measuring, and monitoring nucleic acid transfer results (transfer to which tissues, duration of expression, etc.). The types of expression systems and reporter genes that can be used or adapted for use are well known in the art. For example, genes coding for a luciferase activity, an alkaline phosphatase activity, or a green fluorescent protein activity are commonly used.

The nucleic acid may contain any nucleotide sequence of any size. The nucleic acid may thus vary in size from a simple oligonucleotide to a larger molecule such as a nucleotide sequence including exons and/or introns and/or regulatory elements of any sizes (small or large), a gene of any size, for example of large size, or a chromosome for instance, and may be a plasmid, an episome, a viral genome, a phage, a yeast artificial chromosome, a minichromosome, an antisense molecule, etc.

In some embodiments, the nucleic acid is a double-stranded, circular DNA, such as a plasmid, encoding a product with biological activity.

The nucleic acid can be prepared and produced according to conventional recombinant DNA techniques, such as amplification, culture in prokaryotic or eukaryotic host cells, purification, etc. The techniques of recombinant DNA technology are known to those of ordinary skill in the art.

In embodiments, the therapeutic nucleic acids include nucleic acids encoding proteins and RNAs, including siRNAs. Such therapeutic nucleic acids may act by providing an activity that is missing, or significantly reduced, in a diseased eye. Such molecules may also act by modifying or reducing an activity that is over-expressed, or significantly elevated above normal levels, in a diseased eye. For example, a therapeutic nucleic acid may encode a protein possessing an activity (e.g., specific binding activity, enzymatic activity, transcriptional regulation activity, etc.) that is lacking in cells of the eye. Lack of such activity may result from failure of the cells to produce the protein, production of a mutated, inactive form of the protein, or misfolding of a protein resulting in an inactive form. In some cases, introducing a "good" (i.e., functional) copy of the protein may alleviate symptoms of the disease by directly replacing the missing activity. Alternatively, therapeutic nucleic acids may act by increasing or decreasing the activity of other proteins in cells of the eye. For example, the therapeutic nucleic acid may encode a protein that may bind to another protein and thereby either decrease, or eliminate the activity of the second protein. Alternatively, binding of the therapeutic nucleic acid may encode a protein that may bind to another protein in cells of the eye, which may result in stabilization of such protein and/or an increase in the related activity. Finally, the therapeutic nucleic acid may increase or decrease transcription of genes, or the translation of transcripts from genes in cells of the eye. For example, a therapeutic nucleic may encode a protein that may bind to a transcriptional region of a gene and thereby increase or decrease transcription of that gene.

The down regulation of gene expression using antisense nucleic acids can be achieved at the translational or transcriptional level. Antisense nucleic acids can be nucleic acid fragments capable of specifically hybridizing with a nucleic acid encoding an endogenous ocular active substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous ocular active substance. Antisense nucleic acids can be prepared by expression of all or part of a nucleic acid encoding an endogenous ocular active substance, in the opposite orientation. Any length of antisense sequence is suitable for practice of the invention so long as it is capable of down-regulating or blocking expression of the endogenous ocular active substance. Preferably, the antisense sequence is at least 20 nucleotides in length. The preparation and use of antisense nucleic acids, DNA encoding antisense RNAs and the use of oligo and genetic antisense is disclosed in WO92/15680, the content of which is incorporated herein by reference.

In some embodiments, the nucleic acid encodes or is an interfering RNA (RNAi) or antisense polynucleotide sequences useful in eliminating or reducing the production of a gene product, as described by Tso, P. et al Annals New York Acad. Sci. 570:220-241 (1987). Typically, RNAi include RNAi that decrease the level of an apoptotic or angiogenic factor in a cell.

In some embodiments the nucleic acid is siRNA. siRNAs are double stranded RNA molecules (dsRNAs) with approximately 20 to 25 nucleotides, which are generated by the cytoplasmic cleavage of long RNA with the RNase III enzyme Dicer. siRNAs specifically incorporate into the RNA-induced silencing complex (RISC) and then guide the RNAi machinery to destroy the target mRNA containing the complementary sequences. Since RNAi is based on nucleotide base-pairing interactions, it can be tailored to target any gene of interest, rendering siRNA an ideal tool for treating diseases with gene silencing. Gene silencing with siRNAs has a great potential for the treatment of human diseases as a new therapeutic modality. Numerous siRNAs have been designed and reported for various therapeutic purposes and some of the siRNAs have demonstrated specific and effective silencing of genes related to human diseases. Therapeutic applications of siRNAs include, but are not limited to, inhibition of viral gene expression and replication in antiviral therapy, anti-angiogenic therapy of ocular diseases, treatment of autoimmune diseases and neurological disorders, and anticancer therapy. Therapeutic gene silencing has been demonstrated in mammals, which bodes well for the clinical application of siRNA. It is believed that siRNA can target every gene in human genome and has unlimited potential to treat human disease with RNAi.

For example, an RNAi can be a shRNA or siRNA that reduces the level of a polynucleotide product that induces or promotes apoptosis in a cell. Genes whose polynucleotide products induce or promote apoptosis are referred to herein as "pro-apoptotic genes" and the products of those genes (mRNA; protein) are referred to as "pro-apoptotic polynucleotide products." Pro-apoptotic polynucleotide products include, e.g., Bax, Bid, Bak, and Bad polynucleotide products. See, e.g., U.S. Pat. No. 7,846,730. Interfering RNAs could also be against an angiogenic product, for example VEGF (e.g., CandS; see, e.g., U.S. Patent Publication No. 2011/0143400; U.S. Patent Publication No. 2008/0188437; and Reich et al. (2003) Mol. Vis. 9:210), VEGFR1 (e.g., Sirna-027; see, e.g., Kaiser et al. (2010) Am. J. Ophthalmol. 150:33; and Shen et al. (2006) Gene Ther. 13:225), or VEGFR2 (Kou et al. (2005) Biochem. 44: 15064). See also, U.S. Pat. Nos. 6,649,596, 6,399,586, 5,661,135, 5,639,872, and 5,639,736; and U.S. Pat. Nos. 7,947,659 and 7,919,473.

In some embodiments, the therapeutic nucleic acids can encode biologically active polypeptides or proteins including enzymes, blood derivatives, hormones, lymphokines, cytokines, chemokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, in particular soluble receptors, a peptide which is an agonist or antagonist of a receptor or of an adhesion protein, antigens, antibodies, fragments or derivatives thereof and other essential constituents of the cell, proteins involved in the visual cycle within RPE cells, and structure proteins of retinal cells (structure proteins, proteins involved in the phototransduction process and/or in the visual cycle; retinal recycling) and/or phagocytosis of the photoreceptor outer segment phagocytosis).

Various retina-derived neurotrophic factors have the potential to rescue degenerating photoreceptor cells, and may be delivered trough a method according to the present invention. Preferred biologically active agents may be selected from VEGF, Angiogenin, Angiopoietin-1, DeM, acidic or basic Fibroblast Growth Factors (aFGF and bFGF), FGF-2, Follistatin, Granulocyte Colony-Stimulating factor (G-CSF), Hepatocyte Growth Factor (HGF), Scatter Factor (SF), Leptin, Midkine, Placental Growth Factor (PGF), Platelet-Derived Endothelial Cell Growth Factor (PD-ECGF), Platelet-Derived Growth Factor-BB (PDGF-BB), Pleiotrophin (PTN), RdCVF (Rod-derived Cone Viability Factor), Progranulin, Proliferin, Transforming Growth Factor-alpha (TGF-alpha), PEDF, Transforming Growth Factor-beta (TGF-beta), Tumor Necrosis Factor-alpha (TNF-alpha), Vascular Endothelial Growth Factor (VEGF), Vascular Permeability Factor (VPF), CNTF, BDNF, GDNF, PEDF, NT3, BFGF, angiopoietin, ephrin, EPO, NGF, IGF, GMF, aFGF, NTS, Gax, a growth hormone, [alpha]-1-antitrypsin, calcitonin, leptin, an apolipoprotein, an enzyme for the biosynthesis of vitamins, hormones or neuromediators, chemokines, cytokines such as IL-1, IL-8, IL-10, IL-12, IL-13, a receptor thereof, an antibody blocking any one of said receptors, TIMP such as TIMP-1, TIMP-2, TIMP-3, TIMP-4, angioarrestin, endostatin such as endostatin XVIII and endostatin XV, ATF, angiostatin, a fusion protein of endostatin and angiostatin, the C-terminal hemopexin domain of matrix metalloproteinase-2, the kringle 5 domain of human plasminogen, a fusion protein of endostatin and the kringle 5 domain of human plasminogen, the placental ribonuclease inhibitor, the plasminogen activator inhibitor, the Platelet Factor-4 (PF4), a prolactin fragment, the Proliferin-Related Protein (PRP), the antiangiogenic antithrombin III, the Cartilage-Derived Inhibitor (CDI), a CD59 complement fragment, C3a and C5a inhibitors, complex attack membrane inhibitors, Factor H, ICAM, VCAM, caveolin, PKC zeta, junction proteins, JAMs, CD36, MERTK vasculostatin, vasostatin (calreticulin fragment), thrombospondin, fibronectin, in particular fibronectin fragment gro-beta, an heparinase, human chorionic gonadotropin (hCG), interferon alpha/beta/gamma, interferon inducible protein (IP-10), the monokine-induced by interferon-gamma (Mig), the interferon-alpha inducible protein 10 (IP10), a fusion protein of Mig and IP10, soluble Fms-Like Tyrosine kinase 1 (FLT-1) receptor, Kinase insert Domain Receptor (KDR), regulators of apoptosis such as Bcl-2, Bad, Bak, Bax, Bik, BcI-X short isoform and Gax, fragments or derivatives thereof and the like.

In some embodiments, the biologically active nucleic acid encodes a precursor of a therapeutic protein such as those described above.

In some embodiments, the nucleic acid may encode for a viable protein so as to replace the defective protein which is naturally expressed in the targeted tissue. Typically, defective genes that may be replaced include, but are not limited to, genes that are responsible for retinal degenerative diseases such as retinitis pigmentosa (RP), Leber congenital amaurosis (LCA), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alstrom syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, and Birdshot Retinochoroidopathy. Examples of genes include but are not limited to genes encoding for ATP-binding cassette transporter, RPE65, RdCVF, CP290.

In other embodiments, the nucleic acid encodes a site-specific endonuclease that provides for site-specific knockdown of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease (such as TALEnucleases, meganucleases or Zinc finger nucleases) can be targeted to the defective allele and knock out the defective allele. In addition to knocking out a defective allele, a site-specific nuclease can also be used to stimulate homologous recombination with a donor DNA that encodes a functional copy of the protein encoded by the defective allele. Thus, e.g., the method of the invention can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) Nature 475:217. In some embodiments, the vector comprises a polynucleotide that encodes a site-specific endonuclease; and a polynucleotide that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, and the like. Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

The nucleic acid can be complexed to the carrier compounds described herein by admixing the nucleic acid and the compound or corresponding disulfide oligomer or polymer. The pH of the reaction can be modified to convert the amino groups present on the compounds described herein to cationic groups. For example, the pH can be adjusted to protonate the amino group. With the presence of cationic groups on the compound, the nucleic acid can electrostatically bond (i.e., complex) to the compound. In one aspect, the pH is from 1 to 7.4. In another aspect, the N/P ratio is from 0.5 to 100, where N is the number of nitrogen atoms present on the compound that can be form a positive charge and P is the number of phosphate groups present on the nucleic acid. Thus, by modifying the compound with the appropriate number of amino groups in the head group, it is possible to tailor the bonding (e.g., type and strength of bond) between the nucleic acid and the compound. The N/P ratio can be adjusted depending on the cell type to which the nucleic acid is to be delivered. In some embodiments where the cell is cancer, the N/P ratio can be at least about 6, at least about 10, or at least about 15. In other embodiments, the N/P ration can be from about 6 to about 20.

In one aspect, the nucleic acid/carrier complex is a nanoparticle. In one aspect, the nanoparticle has a diameter of about 1000 nanometers or less.

In other aspects, the compounds described herein can be designed so that the resulting nucleic acid nanoparticle escapes endosomal and/or lysosomal compartments at the endosomal-lysosomal pH. For example, the compound forming nanoparticles with nucleic acids can be designed such that its structure and amphiphilicity changes at endosomal-lysosomal pH (5.0-6.0) and disrupts endosomal-lysosomal membranes, which allows entry of the nanoparticle into the cytoplasm. In one aspect, the ability of specific endosomal-lysosomal membrane disruption of the compounds described herein can be tuned by modifying their pH sensitive amphiphlicity by altering the number and structure of protonatable amines and lipophilic groups. For example, decreasing the number of protonatable amino groups can reduce the amphiphilicity of a nanoparticle produced by the compound at neutral pH. In one aspect, the compounds herein have 1 to 50, 1 to 40, 1 to 30, 1 to 20, 1 to 10, 1 to 8, 1 to 6, 1 to 4, or 2 protonatable amino or substituted amino groups. The pH-sensitive amphiphilicity of the compounds and nanoparticles produced by the compounds can be used to fine-tune the overall pKa of the nanoparticle. Low amphiphilicity of the nanoparticles at physiological pH can minimize non-specific cell membrane disruption and nonspecific tissue uptake of the nucleic acid/MFC system. In certain aspects, it is desirable that the carriers have low amphiphilicity at the physiological pH and high amphiphilicity at the endosomal-lysosomal pH, which will only cause selective endosomal-lysosomal membrane disruption with the nanoparticles.

The surface of the nanoparticle complexes can be modified by, for example, covalently incorporating polyethylene glycol by reacting unpolymerized free thiol of the nanoparticle to reduce non-specific tissue uptake in vivo. For example, PEG-maleimide reacts rapidly with free thiol groups. The molecular weight of the PEG can vary depending upon the desired amount of hydrophilicity to be imparted on the carrier. PEG-modification of the carrier can also protect nanoparticles composed of the nucleic acid from enzymatic degradation upon uptake by the cell (e.g., endonucleases).

In some embodiments, the amount or mole percent of the targeting groups provided on or attached to the surface of the nanoparticle can be about 1 mol % to about 10 mol % of the compounds that form the nanoparticle, for example, about 1 mol % to about 5 mol % (e.g., about 2.5 mol %) of the compounds that form the nanoparticle.

Advantageously, multifunctional pH-sensitive carriers formed using the compounds have improved stability when administered systemically to a subject, protect condensed nucleic acids from degradation, and promote endosomal escape and cytosolic release upon cellular uptake.

The compounds described herein can be used in a method to introduce a nucleic acid into a cell of the eye or a cell delivered to the eye. The method generally involves contacting the cell with a complex, wherein the nucleic acid is taken up into the cell. In one aspect, the compounds described herein can facilitate the delivery of DNA or RNA as therapy for genetic disease by supplying deficient or absent gene products to treat any genetic disease or by silencing gene expression. Techniques known in the art can used to measure the efficiency of the compounds described herein to deliver nucleic acids to a cell.

In some embodiments, the cell can be a cell within the eye. Examples of cells within the eye can include cells located in the ganglion cell layer (GCL), the inner plexiform layer inner (IPL), the inner nuclear layer (INL), the outer plexiform layer (OPL), outer nuclear layer (ONL), outer segments (OS) of rods and cones, the retinal pigmented epithelium (RPE), the inner segments (IS) of rods and cones, the epithelium of the conjunctiva, the iris, the ciliary body, the corneum, and epithelium of ocular sebaceous glands.

The complexes (i.e., nanoparticles) described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular sites and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

The pharmaceutical composition can be administered in a number of ways depending on whether local or systemic treatment is desired, and on the area to be treated. Administration can be topically, including ophthalmically. In the case of contacting cells with the nanoparticle complexes of nucleic acid described herein, it is possible to contact the cells in vivo or ex vivo.

In some embodiments, the complexes (i.e., nanoparticles) are administered to an eye of the subject such that they are able to traverse the outer layers of the eye (i.e., cornea, iris, sclera, pupil, lens, or conjunctiva) and enter into the intraocular fluid (also referred to as the aqueous humor). In other embodiments, the complexes (i.e., nanoparticles) are able to traverse the outer layers of the eye and enter into the intraocular fluid. Thus, in certain embodiments complexes (i.e., nanoparticles) are administered topically to the eye. In some embodiments, the complexes are injected into the eye. This may include intramuscular, intradermal, subcutaneous, subconjunctival and sub-Tenon's, intravitreal, subretinal, intravenous and intracameral injections. Such injections can deliver the complexes to the intraocular fluid or to a location within the retina. In one embodiment, the injection delivers the complexes to the intraocular fluid. In one embodiment, the injection delivers the complexes into the retina. In one embodiment, the complexes are administered by intravitreal injection. In another embodiment, the complexes are administered by subretinal injection. In another embodiment, the complexes are administered by sub-Tenon's injection. Methods of performing intraocular injections are known to those skilled in the art.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. It is understood that any given particular aspect of the disclosed compositions and methods can be easily compared to the specific examples and embodiments disclosed herein, including the reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

The following example is for the purpose of illustration only and is not intended to limit the scope of the claims, which are appended hereto.

Example 1

In this Example, we designed and prepared all-trans-retinylamine modified ECO plasmid DNA (pDNA) nanoparticles with PEG spacer to target interphotoreceptor retinoid-binding protein (IRBP) for enhanced gene delivery in the retina. All-trans-retinoids have a high binding affinity for retinoid binding proteins, which play important roles in visual transduction. IRBP is a major protein in the interphotoreceptor matrix (IPM), and selectively transports 11-cis-retinal to the photoreceptor outer segment and all-trans-retinol to the RPE. This selective transport mechanism can increase the transfection efficiency directly to the RPE with the ECO/pDNA nanoparticles conjugated with all-trans-retinylamine. The in vitro transfection efficiency of the ECO/pDNA nanoparticles was evaluated in ARPE-19, a human RPE cell line. The in vivo transfection efficiency of the targeted ECO/pDNA nanoparticles to the RPE was then evaluated in the wild type BABL/c mice using GFP plasmids. The efficacy of gene therapy of the targeted nanoparticles was determined by ERG in the rpe65$^{-/-}$ mouse model of LCA2.

Materials and Methods

Cell Culture

ARPE-19 cells were cultured in Dulbecco's modified Eagle's medium and supplemented with 10% fetal bovine serum, 100 μg/mL streptomycin, and 100 unites/mL penicillin (all reagents were from Invitrogen, Waltham, Mass.). Cells were maintained in a humidified incubator at 37° C. and 5% $CO_2$.

Animal

BALB/c wild type mice were obtained from Jackson Laboratory (Bar Harbor, Me.). rpe65$^{-/-}$ deficient C57BL6 mice were obtained from Michael Redmond (National Eye Institute, National Institutes of Health, Bethesda, Md.) and genotyped as described previously. All mice were housed and cared for in the animal facility at the School of Medicine, Case Western Reserve University, and animal procedures were approved by CWRU Institutional Animal Care and Use Committee.

Synthesis of Ret-PEG3.4k

Ligand Ret-PEG-3.4k was synthesized through an one-pot reaction. All-trans-retinylamine (15 mg) and MAL-PEG3.4k-SCM (NANOCS, New York, N.Y.) (55 mg) were added to 15 mL dimethylformamide (DMF). The solution was stirred at room temperature overnight. After reaction, product Ret-PEG-3.4k was precipitated in 50 mL diethyl ether and washed for 3 times. The product was dried under vacuum to yield yellow powder Ret-PEG-3.4k. The yield is 89%.

Preparation of ECO/pDNA and Ret-PEG3.4k-ECO/pDNA Nanoparticles

Multifunctional pH-sensitive lipid ECO were synthesized as previously reported. The ECO/pDNA nanoparticles were prepared by a stepwise self-assembly of ECO with plasmid DNA at an amine/phosphate (N/P) ratio of 6. The ECO stock solution (2.5 mM in ethanol) and plasmid DNA stock solution (0.5 mg/mL) at predetermined amounts based on the N/P ratio were diluted into equal volumes with nuclease-free water, mixed and shaken for 30 min at room temperature. The Ret-PEG3.4k solution (0.4 mM in 50% DMSO and water) was then added to the mixture at 2.5 mol % and shaken for another 30 mM for the reaction to occur between maleimide functional group and free thiols on ECO. A different ECO stock solution (25 mM) was used for in vivo formulations. Lipofectamine 2000 (Invitrogen, Waltham, Mass.)/DNA nanoparticles were prepared according to the manufacturer's recommendation.

Transmission Electron Microscope

The morphology of ECO/pDNA (N/P=6/1) and Ret-PEG3.4k-ECO/pDNA (N/P=6/1) nanoparticles were checked with a transmission electron microscope (JEOL JEM2200FS). Samples for TEM were prepared by depositing 20 μL of the particle solution onto a 300-mesh copper grid covered by a thin amorphous carbon film (20 nm) Immediately after deposition, the excess liquid was removed by touching the grid with filter paper. Samples were stained twice by the addition of 3 μL of 2% uranyl acetate aqueous solution. The excess of staining solution was removed again. Samples were dried and images were taken right after.

In Vitro Transfection

ARPE-19 cells were seeded onto 12-well plates at a density of 4×10$^4$ cells per well and allowed to grow for 24 h at 37° C. Transfections were conducted in 10% serum media with the nanoparticles of GFP plasmid DNA (Altogen Biosystems, Las Vegas, Nev.) (catalog number 4060) at a DNA concentration of 1 μg/mL. ECO/pGFP nanoparticles were incubated with ARPE-19 cells for 8 hours at 37° C. The media then was replaced with fresh serum-containing media (10% serum) and cells were then cultured for an additional 48 h. GFP expression was monitored with an Olympus FV1000 confocal microscope (Olympus, Center Valley, Pa.). After the culture media was removed, each well was washed twice with PBS (10 mM sodium phosphate, pH 7.2, and 100 mM NaCl). Cells were harvested after treatment with 0.25% trypsin containing 0.26 mM EDTA (Invitrogen), followed by centrifugation at 1000 rpm for 5 mM, fixation in 750 μL PBS containing 4% paraformaldehyde, and finally passed through a 35 μm cell strainer (BD Biosciences, San Jose, Calif.). A BD FACSCalibur flow cytometer (BD Biosciences) was used to determine GFP expression based on the fluorescence intensity in a total of 10,000 cells for each sample.

Intracellular Trafficking

ARPE-19 cells (4×10$^4$/well) were seeded onto glass-bottom micro-well dishes and allowed to grow for 24 h at 37° C. The cells were stained with 4 μg/mL Hoechst 33342 (Invitrogen) and 100 mM LysoTracker Green (Life Technologies, Carlsbad, Calif.). Cells were then treated with ECO/Cy3-pDNA (Mirus Bio LLC, Madison, Wis.) (catalog number MIR7904) (N/P ratio 6/1) nanoparticles in 10% serum media. Cells were cultured with nanoparticles for 1 h, 4 h and 24 h (media was replaced by fresh media after 4 h), when the medium was removed and they were washed with PBS for three times before fixation with PBS containing 4% paraformaldehyde. Fluorescence images were taken with an Olympus FV1000 confocal microscope.

In Vivo Subretinal Transfection with ECO/pDNA and Ret-PEG3.4k-ECO/pDNA Nanoparticles All surgical manipulations were carried out under a surgical microscope (Leica M651 MSD). Mice were anesthetized by intraperitoneal injection of 20 μL/g of body weight of 6 mg/mL ketamine and 0.44 mg/mL xylazine in 10 mM sodium phosphate and 100 mM NaCl buffer solution (pH=7.2). Pupils were dilated with 1.0% tropic amide ophthalmic solution (Bausch & Lomb, Rochester, N.Y.). A 33-gauge beveled needle (World Precision Instruments, Sarasota, Fla.) was used as a lance to make a full thickness cut through sclera at 1.0 mm posterior to the limbus. This needle was replaced with a 36-gauge beveled needle attached to an injection system (UMP-II microsyringe pump and a Micro4 controller with a footswitch, World Precision Instruments). This needle was aimed toward the inferior nasal area of the retina, and either an ECO/pDNA or Ret-PEG3.4k-ECO/pDNA nanoparticles solution (2 µL) was injected at a pRPE65 (Origene, Rockville, Md.) (catalog number SC119977) or pGFP dose of 200 ng into the subretinal space. Successful administration was confirmed by observing bleb formation. The tip of the needle remained in the bleb for 10 s after bleb formation, when the needle was gently withdrawn. A solution (2 µL) of Ret-PEG3.4k-ECO carrier alone with the same concentration as Ret-PEG3.4k-ECO/pDNA nanoparticles was also injected into the subretinal space of the contra eye served as a control (vehicle injected). To check GFP expression 3 days after injection, eyes were collected, washed with penicillin-streptomycin solution (Sigma), and rinsed with Hanks' balanced salt solution (Hyclone, Waltham, Mass.). Eye cups were prepared as previously described. The retina and RPE layers were placed in glass bottom confocal plate and fixed with 1 mL of PBS with 4% paraformaldehyde. An Olympus FV1000 confocal microscope was used to assess GFP expression as noted above.

Quantitative RT-PCR (qRT-PCR)

Total RNA was isolated from the eyes of rpe65 mice 15 days after subretinal injection with Ret-PEG3.4k-ECO/pRPE65 nanoparticles. cDNA was synthesized with the QuantiTect Reverse Transcription Kit (Qiagen) following the manufacturer's instructions. Quantitative RT-PCR amplification was performed using SYBR Green I Master mix (Roche Diagnostics, Risch-Rotkreuz, Switzerland). Fold changes were calculated after normalizing the data to Glyceraldehyde 3-phosphate dehydrogenase. Rpe65$^{-/-}$ mice with no treatment were used as control group.

Electroreinograms

Electroretinograms were acquired as previously described. Animals were anesthetized by intraperitoneal injection of a cocktail (15 µL/g body weight) comprised of ketamine (6 mg/mL) and xylazine (0.44 mg/mL) in PBS buffer (10 mM sodium phosphate, pH 7.2, and 100 mM NaCl). Pupils were dilated with 1% tropicamide for imaging. Experiments were performed in a dark room. Three electrodes were placed on the animal: a contact lens electrode on the eye, a reference electrode underneath the skin between the ears, and a ground electrode underneath the skin of the tail. Electroretinograms were recorded with the universal electrophysiologic system UTAS E-3000 (LKC Technologies, Inc., Gaithersburg, Md., USA). Light intensity calibrated by the manufacturer was computer-controlled.

Histology

The eye cups for histology were fixed in 2% glutaraldehyde, 4% paraformaldehyde and processed for visualization by OCT (optimum cutting temperature formulation). Sections were cut at 1 µm. Slides samples were permeabilized and fixed sequentially with 4% PFA and 0.25% Triton X-100 followed by blocking with 0.5% BSA blocking solution for 1 h at room temperature. PNA-lectin were applied at a concentration of 12.5 µg/mL for 1h at room temperature and washed 3 times with a 0.1% TBST (tris-buffered saline with tween 20) for 5 min each wash. Slides were counter-stained with DAPI and mounted with coverslip using the Prolong Gold regent (Invitrogen) before imaging. Stained tissue was imaged with an Olympus FV1000 confocal microscope.

Statistical Analysis

Experiments were performed in triplicate and presented as the means and standard deviations. Statistical analysis was conducted with two-tailed Student's t-tests using a 95% confidence interval. Statistical significance was accepted when $p \leq 0.05$.

Results

In Vitro Transfection of ECO/pDNA Nanoparticles

To determine the transfection efficiency of ECO in vitro, human RPE cells (ARPE-19) were transfected with ECO/pGFP (N/P=6/1) nanoparticles, and GFP expression was determined 48 h after transfection by confocal microscopy (FIGS. 1A, B). ECO/pGFP nanoparticles produced significant GFP expression with 69.7% cells expressing GFP, while the control lipofectamine transfected only 14.4% cells as determined by flow cytometry (FIG. 1B). High gene expression efficiency of ECO/pDNA nanoparticles was correlated to their efficient intracellular uptake. FIG. 1C shows the intracellular uptake of ECO/pDNA nanoparticles as imaged by 3D confocal microscopy at 1, 4 and 24 h post transfection with Cy3-pDNA as the tracker. After 1 h incubation, ECO/Cy3-pDNA nanoparticles (red) were aligned at the surface of the cell membrane, due to their positively charged electrostatic interactions with the negatively charged cell membrane. After 4 h, the nanoparticles entered the cell and co-localized with late endosomes, indicated by the yellow color. After 24 h, almost all the nanoparticles escaped endosomal entrapment, shown by the red fluorescence in the cytoplasm and the diminished overlap with the endosomes. The efficient cytosolic pDNA delivery of ECO/pDNA nanoparticles resulted in high gene expression efficiency in the RPE cells in vitro.

Preparation of Retinylamine Targeted ECO/pDNA Nanoparticles

To target IRBP, an all-trans-retinoid structure was introduced into the surface of ECO/pDNA nanoparticles via a PEG (3.4) spacer. All-trans-retinylamine (Ret-NH$_2$) was first reacted with the NHS activated ester of NHS-PEG-Mal to yield a Ret-PEG-Mal, which was confirmed by MALDI-TOF mass spectroscopy (FIGS. 2A, B). To form targeted ECO/pDNA nanoparticles, Ret-PEG-Mal first reacted with the 2.5 mol-% ECO via Michael addition between the thiol and maleimide. The targeted nanoparticles were then formed by self-assembly with pDNA. FIGS. 2C, D show the transmission electron microscopic images of the ECO/pDNA nanoparticles and targeted ECO/pDNA nanoparticles. The average size of ECO/pDNA nanoparticles was approximately 100 nm. The average size of Ret-PEG-ECO/pDNA nanoparticles to around 120 nm, a slight increase after surface modification with Ret-PEG.

In Vivo Transfection with Targeted Ret-PEG-ECO/pGFP Nanoparticles in Wild Type BALB/c Mice The Ret-PEG-ECO/pGFP nanoparticles were subretinally injected in BALB/c mice to determine in vivo gene delivery and expression efficiency with GFP as a reporter gene. Significant GFP expression was observed in the RPE flatmounts with both unmodified ECO/pGFP nanoparticles and targeted Ret-PEG-ECO/pGFP nanoparticles 3-days post injection. However, Ret-PEG-ECO/pGFP nanoparticles produced greater GFP expression than ECO/pGFP nanoparticles (FIG. 3A). ZO-1 staining of tight junction proteins in RPE flatmounts further confirmed that the enhanced GFP expression emanated from RPE cells (FIG. 3B).

Gene Replacement Therapy Using Ret-PEG-ECO/pRPE65 Nanoparticles in rpe65$^{-/-}$ Mice Gene therapy with all-trans-retinylamine modified ECO nanoparticles was conducted in rpe65$^{-/-}$ mice, in which RPE65 was completely knocked down. The rpe65$^{-/-}$ mice exhibited the phenotypic features similar to human LCA2 patients. Ret-PEG-ECO/pRPE65 nanoparticles were injected into the subretinal space of 1-month-old rpe65$^{-/-}$ mice. At 15-days post injection, the treatment with Ret-PEG-ECO/pRPE65 nanoparticle produced higher mRNA levels in the treated group than in the untreated control group (FIG. 4A). This finding demonstrates the successful introduction of the therapeutic gene. Electroretinography (ERG) was performed at the intensity of 1.6 log cdxs/m$^2$ to determine the efficacy of the nanoparticle treatment based on the electrical responses to light from the retina. FIG. 4B shows a significant scotopic and photopic ERG response waveforms in the nanoparticle treatment group at 7 days post-treatment, whereas there was almost no response in control group injected with Ret-PEG-ECO. The amplitudes of the major waves from all ERG tests were calculated at 3, 7, 30, and 120 days post-treatment (FIGS. 4C-F). Significant increase in amplitudes of scotopic a-waves and b-waves were observed for nanoparticle treatment groups, but not for control groups (vehicle injected). The introduction of exogenous RPE65 gene increased about 50% of the scotopic ERG amplitude throughout all time points up to 120 days (FIGS. 4C, E), which demonstrated an improved function of rod photoreceptors. The cone function also improved, represented by a five-fold increase in photopic b-wave amplitude after 3 days and a three-fold increase after 7 days. Although the amplitude decreased with later time points, the photopic b-wave amplitude of the treatment group was double that of the control, even at 120 days. Photopic a-waves were higher in the treatment groups than in the controls, but the difference was not statistically significant.

Cone Preservation after Gene Replacement Therapy Using Ret-PEG-ECO/pRPE65 Nanoparticles in rpe65$^{31\ /-}$ Mice To determine whether Ret-PEG-ECO/pRPE65 nanoparticles could recue cone cells in rpe65$^{-/-}$ mice, cryo-sections of the whole retina were prepared at 120 post-injection and cone cells were stained with peanut agglutinin (green). Compared with the control group (FIG. 5A), the treatment group (FIG. 5B) showed substantial green fluorescence staining, which represented a greater number of healthy cone photoreceptors. This result also explained the increase of photopic wave amplitudes in ERG. Interestingly, fewer cone cells were observed away from injection site (FIG. 5C), suggesting a local rescue in this gene therapy approach.

Therapeutic Effect of Gene Replacement Therapy Using Ret-PEG-ECO/pRPE65 Nanoparticles in 3-month-old rpe65$^{-/-}$ Mice In order to determine the optimal timing for gene replacement therapy of LCA2 with the targeted nanoparticles, we initiated RPE65 gene therapy with Ret-PEG-ECO/pRPE65 nanoparticles in 3-month-old rpe65$^{-/-}$ mice, and ERG tests were performed to evaluate therapeutic efficacy. According to the ERG responses measured at 7 and 30 days post-treatment, no differences were observed for scotopic and photopic waveforms between the treatment and control groups (FIG. 6), demonstrating no observable improvement of eye function. The result suggest that gene replacement therapy with the targeted nanoparticles in these older mice was not as effective in restoring vision as in the younger mice, likely due to the progression of irreversible retinal degeneration in the former age group.

Safety Assessment of Ret-PEG-ECO/pRPE65 Nanoparticles in BALB/c Mice

To evaluate the safety of Ret-PEG-ECO/pRPE65 nanoparticles in gene therapy, the nanoparticles were injected into the subretinal space of healthy 1-month-old BALB/c mice and ERG tests were conducted at 7 and 30 post-injection. ERG responses for both the nanoparticle injected group and the un-injected group were comparable at each light intensity (FIG. 7A). A slight decrease in response amplitudes was observed for some major waveforms at 7 days because of the inflammation introduced by subretinal injection. Eye function after nanoparticle injection became normal at 30 days and no deleterious effects were introduced in the ERG major wave amplitudes (FIG. 7B-E). The result indicates that Ret-PEG-ECO/pRPE65 nanoparticles are safe for subretinal injection in gene replace therapy.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A compound comprising formula (I):

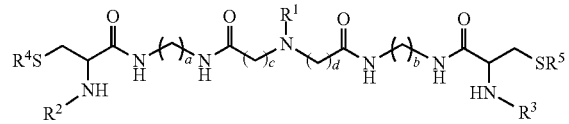

wherein R1 is an alkylamino group or a group containing at least one aromatic group;

R2 and R3 are independently an aliphatic group or a hydrophobic group;

R4 and R5 are independently H, a substituted or unsubstituted alkyl group, an alkenyl group, an acyl group, or an aromatic group, or a polymer, a targeting group, or a detectable moiety, and at least one of R$^4$ or R$^5$ is a retinoid or retinoid derivative that targets and/or binds to an interphotoreceptor retinoid binding protein, wherein upon administration of the compound to an eye of a subject, the retinoid or retinoid derivative enhances transfection efficiency of the compound to retinal pigment epithelium of the eye;

a, b, c, and d are independently an integer from 1 to 10; and pharmaceutically acceptable salts thereof.

2. The compound of claim 1, wherein R$^1$ comprises at least one of:

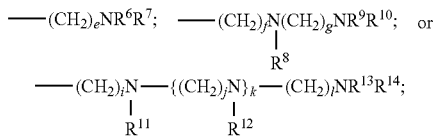

where R$^6$, R$^7$, R$^8$, R$^9$, R$^{10}$, R$^{11}$, R$^{12}$, R$^{13}$, and R$^{14}$ are independently hydrogen, an alkyl group, a hydrophobic group, or a nitrogen containing substituent; and e, f, g, i, j, k, and l, are an integer from 1 to 10.

3. The compound of claim 1, wherein R$^2$ and R$^3$ are independently a hydrophobic group derived from oleic acid or linoleic acid.

4. The compound of claim 3, wherein R$^2$ and R$^3$ are the same.

5. The compound of claim 1, wherein at least one of R$^4$ or R$^5$ is all-trans-retinylamine or (1R)-3-amino-1-[3-(cyclohexylmethoxy)phenyl]propan-1-ol.

6. The compound of claim 1, wherein a, b, c, and d are each 2.

7. The compound of claim 1, $R^1$ comprises at least one of $CH_2CH_2NH_2$, $CH_2CH_2NHCH_2CH_2NHCH_2CH_2NH$, or $CH_2CH_2NHCH_2CH_2CH_2CH_2NHCH_2CH_2CH_2NH$.

8. The compound of claim 1, wherein the targeting group is covalently attached to a thiol group of a cysteine residue by a linker.

9. The compound of claim 8, wherein the linker comprises a polyamino acid group, a polyalkylene group, or a polyethylene glycol group.

10. The compound of claim 9, wherein the linker comprises an acid labile bond.

11. A nanosized complex comprising a nucleic acid and a compound comprising formula (I):

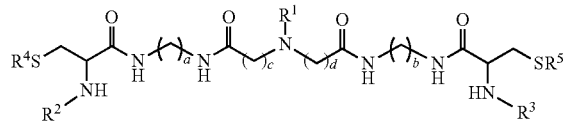

wherein $R^1$ is an alkylamino group or a group containing at least one aromatic group;
$R^2$ and $R^3$ are independently an aliphatic group or a hydrophobic group;
$R^4$ and $R^5$ are independently H, a substituted or unsubstituted alkyl group, an alkenyl group, an acyl group, or an aromatic group, or a polymer, a targeting group, or a detectable moiety, wherein at least one of $R^4$ or $R^5$ is a retinoid or retinoid derivative that targets and/or binds to an interphotoreceptor retinoid binding protein, wherein upon administration of the complex to an eye of a subject, the retinoid or retinoid derivative enhances transfection efficiency of the complex to retinal pigment epithelium of the eye;
a, b, c, and d are independently an integer from 1 to 10; and pharmaceutically acceptable salts thereof.

12. The complex of claim 11, wherein the nucleic acid comprises a natural or synthetic oligonucleotide, a DNA or fragment thereof, or an RNA or fragment thereof.

13. The complex of claim 11, wherein the nucleic acid comprises a siRNA or plasmid DNA.

14. The complex of claim 11, wherein the nucleic acid when introduced to or within the eye is capable of treating, ameliorating, attenuating, and/or eliminating symptoms of a disease or disorder of the eye.

15. The complex of claim 11, the nucleic acid comprising plasmid DNA encodes RPE-65.

16. The complex of claim 11, having an N/P ratio of at least about 6.

17. The complex of claim 12, wherein at least one of $R^4$ or $R^5$ is all-trans-retinylamine or (1R)-3-amino-1-[3-(cyclohexylmethoxy)phenyl]propan-1-ol.

18. The complex of claim 11, wherein the targeting group is covalently attached to a thiol group of a cysteine residue by a linker.

\* \* \* \* \*